United States Patent [19]

Pfirmann et al.

[11] Patent Number: 5,744,628
[45] Date of Patent: Apr. 28, 1998

[54] PROCESS FOR THE PREPARATION OF ESTERS OF AROMATIC CARBOXYLIC ACIDS

[75] Inventors: Ralf Pfirmann, Griesheim; Theodor Papenfuhs, Frankfurt, both of Germany

[73] Assignee: Hoechst Aktiengesellschaft, Frankfurt, Germany

[21] Appl. No.: 681,635

[22] Filed: Jul. 29, 1996

[30] Foreign Application Priority Data

Jul. 31, 1995 [DE] Germany .................. 195 27 996.4
May 20, 1996 [DE] Germany .................. 196 20 191.8

[51] Int. Cl.$^6$ .................. C07C 229/00; C07C 69/76; C07C 67/72
[52] U.S. Cl. .................. 560/19; 560/45; 560/47; 560/55; 560/56; 560/64; 560/65; 560/67; 560/71; 560/103
[58] Field of Search .................. 560/64, 19, 103, 560/45, 55, 56, 71, 65, 67

[56] References Cited

U.S. PATENT DOCUMENTS 5,047,538  9/1991  Domagala et al. .
5,424,479  6/1995  Müller et al. .................. 560/64

FOREIGN PATENT DOCUMENTS 0 640 582  3/1995  European Pat. Off. .

OTHER PUBLICATIONS

Barry, J., et al, *Synthesis*: 40–45 (1985).
Beyer–Walter's Lehrbuch der Organischen Chemie [Textbook of Organic Chemistry], 21st Ed., S. Hirzel Verlag, Stuttgart, 1988, pp. 551, 553 & 559.

*Drugs of the Future* 18:717–720 (1993).

Synthesis; Jan. 1, 1985; pp. 40–45; J. Barry et al.: "Solid–Liquid–Phase–Transfer Catalysis without added Solvent. A Simple, Efficient, and Inexpensive Synthesis of Aromatic Carboxylic Esters by Alkylation of Potassium Carboxylates".

*Primary Examiner*—Paul J. Killos
*Attorney, Agent, or Firm*—Connolly and Hutz

[57] ABSTRACT

The present invention relates to a process for the preparation of compounds of the formula (1)

$$R^1R^2R^3R^4R^5ArCOOR \qquad (1)$$

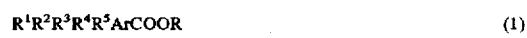

in which $R^1$, $R^2$, $R^3$, $R^4$ and $R^5$ are identical or different and are hydrogen, a halogen, an alkyl or alkoxy group having 1 to 6 carbon atoms, OR, NHR, NR$_2$, SR or COOR, R being an alkyl radical having 1 to 4 carbon atoms, Ar is an aryl radical having 6 to 12 carbon atoms and the radical R identified in formula (1) has the above meaning, by reacting a compound of the formula (2)

$$R^1R^2R^3R^4R^5ArCOOH \qquad (2)$$

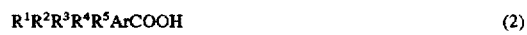

in which $R^1$, $R^2$, $R^3$, $R^4$ and $R^5$ are identical or different and are hydrogen, a halogen, an alkyl or alkoxy group having 1 to 6 carbon atoms, OH, NH$_2$, NHR, SH or COOH and Ar has the same meaning as in formula (1), with a sulfate of the formula (RO)$_2$SO$_2$, in which R has the above meaning, at a pH from 5 to 12 in the presence of a water-insoluble tertiary amine and water at a temperature from 10° to 120° C. in the presence or absence of a water-insoluble solvent and with addition of a base.

30 Claims, No Drawings

PROCESS FOR THE PREPARATION OF ESTERS OF AROMATIC CARBOXYLIC ACIDS

The present invention relates to a process for the preparation of esters of aromatic carboxylic acids by alkylation of aromatic carboxylic acids which optionally contain further alkylatable substituents.

On account of their versatile properties, esters of aromatic carboxylic acids have gained great industrial importance. They can be used in different areas. Salicylic acid esters are used as aromatic substances. Phthalic acid esters of higher alcohols are employed as plasticizers for polyvinyl chloride (PVC) and phthalic acid esters of polyhydric alcohols are used for preparation of raw materials for varnishes or lacquers. Some esters of p-aminobenzoic acid, for example ethyl p-aminobenzoate (Anesthesin) or β-diethylaminoethyl p-aminobenzoate (procaine) have proven useful in the form of their hydrochlorides as local anesthetics (Beyer-Walter, Lehrbuch der organischen Chemie [Textbook of organic chemistry], 21st Edition, pages 553, 559 and 551; S. Hirzel Verlag Stuttgart 1988). Esters of fluorinated benzoic acids, for example esters of 2,3,4,5-tetrafluorobenzoic acid (Drugs of the future 1993, Volume 18 Issue 8, pages 717 to 720) or the methyl ester of 3-methoxy-2,4,5-trifluorobenzoic acid (U.S. Pat. No. 5,047, 538), can be used as precursors for the preparation of antibacterial agents from the fluoroquinolonecarboxylic acids series or be converted into further precursors needed for the preparation of these antibacterial agents.

Carboxylic acid esters can mainly be prepared in two ways:

1. By esterification of the carboxylic acids with an excess of alcohol under acidic conditions, water being eliminated.
2. By alkylation of a carboxylic acid salt by means of an alkylating agent, for example an alkyl halide. In this process, the carboxylic acid salt is customarily used in the form of an aqueous solution prepared by reaction of the carboxylic acid with an aqueous base or prepared in situ by reaction of the carboxylic acid with a base dissolved in water.

In Synthesis (1985), 40–45, J. Barry describes a preparation of aromatic carboxylic acid esters by alkylation of potassium salts of aromatic carboxylic acids without addition of a solvent, but using a phase-transfer catalyst. Beside alkyl halides, dimethyl sulfate and diethyl sulfate are employed as alkylating agents.

The potassium carboxylate is prepared either by dissolution of the carboxylic acid in the stoichiometric amount of an aqueous potassium hydroxide solution, subsequent evaporation of the water and grinding of the dry potassium carboxylate to give a fine powder (method A) or by mixing of finely divided carboxylic acid, finely divided potassium hydroxide and the ammonium salt employed as phase-transfer catalyst, by subsequent heating of this mixture to 140° C. and final grinding of the fusion residue (method B).

The potassium carboxylate prepared by method A is treated with the phase-transfer catalyst and then with the alkylating agent, for example dimethyl sulfate, while the potassium carboxylate prepared by method B, which already contains the phase-transfer catalyst, is treated directly with the alkylating agent.

The mixture is shaken, reacted under the reaction conditions indicated, then diluted twice with ether, filtered through a short column packed with an aid and then purified by chromatography or crystallization.

Aromatic carboxylic acids which optionally contain further alkylatable substituents can also be reacted by this method, using, for example, dimethyl sulfate.

The process described above has several disadvantages. On the one hand, both the potassium carboxylate prepared by method A and by method B requires a considerable expenditure of energy, for example the evaporation of water and the mechanical grinding of the carboxylic acid, the potassium hydroxide and the potassium carboxylate residue. On the other hand, the working-up of the reaction mixture obtained (dilution with ether two times, filtration and subsequent purification by column chromatography or crystallization) proves to be very laborious.

Moreover, the ammonium salts used as phase-transfer catalyst pass into the effluent, pollute it and, as they are difficult to break down, lead to problems in processing the effluent.

It is thus a worthwhile object to provide a process for the preparation of aromatic carboxylic acid esters which does not have the disadvantages outlined above and which additionally permits, beside the alkylation of the carboxyl group, further alkylatable substituents to be alkylated as well.

This object is achieved by a process for the preparation of compounds of the formula (1)

$$R^1R^2R^3R^4R^5ArCOOR \tag{1}$$

in which $R^1$, $R^2$, $R^3$, $R^4$ and $R^5$ are identical or different and are hydrogen, a halogen, an alkyl or alkoxy group having 1 to 6 carbon atoms, OR, NHR, NR$_2$, SR or COOR, R being an alkyl radical having 1 to 4 carbon atoms, Ar is an aryl radical having 6 to 12 carbon atoms and the radical R identified in formula (1) has the above meaning. It comprises reacting a compound of the formula (2)

$$R^1R^2R^3R^4R^5ArCOOH \tag{2}$$

in which $R^1$, $R^2$, $R^3$, $R^4$ and $R^5$ are identical or different and are hydrogen, a halogen, an alkyl or alkoxy group having 1 to 6 carbon atoms, OH, NH$_2$, atoms, OH, NH$_2$, NHR, SH or COOH and Ar has the same meaning as in formula (1), with a sulfate of the formula (RO)$_2$SO$_2$, in which R has the above meaning, at a pH from 5 to 12 in the presence of a water-insoluble tertiary amine and water at a temperature from 10° to 120° C. in the presence or absence of a water-insoluble solvent and with addition of a base.

The process according to the invention has several advantages.

On the one hand, it is not necessary to employ the aromatic carboxylic acid to be reacted in the form of its anhydrous potassium salt, but it is sufficient to prepare an aqueous solution of a salt of the aromatic carboxylic acid in situ from the aromatic carboxylic acid. On the other hand, in a large number of cases it is unnecessary to employ a phase-transfer catalyst which is difficult to break down. By this means, pollution of the effluent and trouble with the working-up of the effluent are also avoided.

A further advantage consists in having to separate from the aqueous phase, after completion of the reaction, only the organic phase which contains the water-insoluble tertiary amine and the useful product. Further working-up is generally carried out by distillation. By this means the use of a problematic solvent, for example ether, is avoided.

Moreover, it is to be regarded as surprising that the water-insoluble tertiary amine does not react with the dialkyl sulfate at all or only to a very small extent. This results in the process according to the invention not leading to an increased consumption of dialkyl sulfate.

It is also an advantage that, after separation of the useful product, i.e. the compound of the formula (1), the remaining water-insoluble tertiary amine can be employed in the reaction again. As a result, the need for auxiliaries, which can lead to additional pollution of the effluent, is kept low.

The process according to the invention not only makes it possible to alkylate the carboxyl group in the compound of the formula (2), but also further alkylatable groups present in the aromatic carboxylic acid of the formula (2), namely the OH, $NH_2$, NHR, SH and COOH groups. If desired, the alkylation of these groups of differing activity can also be carried out at a single pH. As a result, the process according to the invention turns out to be very simple.

However, the reaction can also be allowed to take place at different pHs, in order to work first at a higher pH and following this at a lower pH. This variant of the process is also very simple to carry out, as the reaction does not have to be interrupted for this purpose, but can be carried out in the same reaction medium.

Customarily, a compound (2), in which $R^1$ and $R^2$ are identical or different and are hydrogen, an alkyl group having 1 to 6 carbon atoms, OH, $NH_2$ or COOH, in particular hydrogen, OH or COOH, is employed.

A compound of the formula (2), in which $R^1$ or $R^2$ is OH or COOH, in particular OH, can also be employed. The other four radicals $R^1$, $R^3$, $R^4$ and $R^5$ or $R^2$, $R^3$, $R^4$ and $R^5$ are identical or different in this case and are hydrogen, a halogen, an alkyl or alkoxy group having 1 to 6 carbon atoms, in particular hydrogen, fluorine, chlorine or an alkyl group having 1 to 6 carbon atoms, preferably hydrogen or fluorine.

In a number of cases, a compound of the formula (2) in which $R^3$, $R^4$ and $R^5$ are identical or different and are hydrogen, a halogen, an alkyl or an alkoxy group having 1 to 6 carbon atoms, in particular hydrogen, fluorine, chlorine or an alkyl group having 1 to 6 carbon atoms, preferably hydrogen or fluorine, can be employed in the reaction.

In the reaction, a compound of the formula (2) is employed in which Ar, as already mentioned at the outset, is an aryl radical having 6 to 12 carbon atoms, in particular a phenyl radical, biphenyl radical or naphthyl radical, preferably a phenyl radical.

Without claiming to be complete, examples of compounds of the formula (2) which may be mentioned are 2-chlorobenzoic acid,
3-chlorobenzoic acid
4-chlorobenzoic acid,
2-fluorobenzoic acid,
3-fluorobenzoic acid,
4-fluorobenzoic acid,
2-bromobenzoic acid,
3-bromobenzoic acid,
4-bromobenzoic acid,
2,4-dichlorobenzoic acid
2,4-difluorobenzoic acid,
3,4-difluorobenzoic acid,
3,4-dichlorobenzoic acid,
2,5-dichlorobenzoic acid,
2,6-difluorobenzoic acid,
2,3,6-trifluorobenzoic acid,
2,4,5-trifluorobenzoic acid,
2,4,5-trichlorobenzoic acid,
2,3,4,5-tetrachlorobenzoic acid,
2,3,4,5-tetrafluorobenzoic acid,
2,3,5,6-tetrafluorobenzoic acid,
pentafluorobenzoic acid,
pentachlorobenzoic acid,
2-chloro-3,4,5-trifluorobenzoic acid,
2,3-dichloro-4,5-difluorobenzoic acid,
2,4,5-trifluoro-3-chlorobenzoic acid,
2,4-difluoro-3,5-dichlorobenzoic acid,
2,6-difluoro-3,5-dichlorobenzoic acid,
2-hydroxybenzoic acid,
3-hydroxybenzoic acid,
4-hydroxybenzoic acid,
2-chloro-4-hydroxybenzoic acid,
2-fluoro-4-hydroxybenzoic acid,
2,3,5-trifluoro-4-hydroxybenzoic acid,
2,4,5-trifluoro-3-hydroxybenzoic acid,
4-hydroxy-2,3,5,6-tetrafluorobenzoic acid,
5-chloro-2-hydroxybenzoic acid,
5-fluoro-2-hydroxybenzoic acid,
4-chloro-2-hydroxybenzoic acid,
5-chloro-2-hydroxybenzoic acid,
4-chloro-2-aminobenzoic acid,
4-fluoro-2-aminobenzoic acid,
5-fluoro-2-aminobenzoic acid,
5-chloro-2-aminobenzoic acid,
3-amino-2,4,5-trifluorobenzoic acid,
4-aminobenzoic acid,
4-amino-2-chlorobenzoic acid,
4-amino-2-fluorobenzoic acid,
4-amino-2,3,5-trifluorobenzoic acid,
6-methyl-3-amino-2,4,5-trifluorobenzoic acid,
3-hydroxy-2,4-difluorobenzoic acid,
4-hydroxy-3-fluorobenzoic acid,
4-hydroxy-3-chlorobenzoic acid,
4-hydroxy-3,5-dichlorobenzoic acid,
4-hydroxy-3,5-difluorobenzoic acid,
3-hydroxytetrafluorobenzoic acid,
2-hydroxytetrafluorobenzoic acid,
3-methyl-2,4,5-trifluorobenzoic acid,
3-ethyl-2,4,5-trifluorobenzoic acid and
6-methyl-3-hydroxy-2,4,5-trifluorobenzoic acid, in particular 2,3,6-trifluorobenzoic acid, 2,4,5-trifluorobenzoic acid, 2,4,5-trichlorobenzoic acid, 2,3,4,5-tetrachlorobenzoic acid, 2,3,4,5-tetrafluorobenzoic acid, 2,3,5,6-tetrafluorobenzoic acid, 2-hydroxybenzoic acid, 3-hydroxybenzoic acid, 4-hydroxybenzoic acid, 2-chloro-4-hydroxybenzoic acid, 2-fluoro-4-hydroxybenzoic acid, 2,3,5-trifluoro-4-hydroxybenzoic acid, 2,4,5-trifluoro-3-hydroxybenzoic acid, 4-hydroxy-2,3,5,6-tetrafluorobenzoic acid, 5-chloro-2-hydroxybenzoic acid, 5-fluoro-2-hydroxybenzoic acid, 4-chloro-2-hydroxybenzoic acid, 5-chloro-2-hydroxybenzoic acid, 3-hydroxy-2,4-difluorobenzoic acid, 4-hydroxy-3-fluorobenzoic acid, 4-hydroxy-3-chlorobenzoic acid, 4-hydroxy-3,5-dichlorobenzoic acid, 4-hydroxy-3,5-difluorobenzoic acid, 3-hydroxytetrafluorobenzoic acid, 2-hydroxytetrafluorobenzoic acid, 6-methyl-3-hydroxy-2,4,5-trifluorobenzoic acid.

The compound of the formula (2) is reacted with a sulfate of the formula $(RO)_2SO_2$ in which R is an alkyl radical having 1 to 4 carbon atoms. The sulfate of the formula $(RO)_2SO_2$ employed is in particular dimethyl sulfate, diethyl sulfate or dibutyl sulfate, preferably dimethyl sulfate or diethyl sulfate.

The reaction is allowed to proceed in the presence of a water-insoluble tertiary amine. The term water-insoluble tertiary amine is understood as meaning those amines which only dissolve in water to a small extent or not at all.

Customarily, the water-insoluble tertiary amine employed is a trialkylamine having 4 to 20 carbon atoms per alkyl radical, a mixture of these trialkylamines, an N-containing heterocyclic compound or a mixture of the above amines, in particular a trialkylamine having 6 to 14 carbon atoms per alkyl radical, a mixture of these trialkylamines, an optionally alkylated pyridine or quinoline, for example collidine, lutidine or a picoline, or a mixture of these tertiary amines. The abovementioned trialkylamines contain straight-chain and/or branched alkyl radicals. The alkyl radicals can be identical or different. Mixtures of the abovementioned trialkylamines are highly suitable.

In a number of cases, a mixture of trialkylamines having 6 to 12 carbon atoms per alkyl radical which contain identical or different straight-chain or branched alkyl radicals has proven particularly suitable.

As the reaction is carried out in the presence of the water-insoluble tertiary amine and water, the reaction takes place in a reaction medium consisting of two liquid phases. In order to promote the reaction, provision is to be made for good mixing of the two phases. After completion of the reaction, the two phases customarily separate such that the separation of the aqueous phase from the organic phase presents no problems.

Without claiming to be complete, water-insoluble trialkylamines of the abovementioned type which may be mentioned are the following compounds:

tri-n-butylamine, triisobutylamine, tri-n-pentylamine, triisopentylamine, tri-n-hexylamine, tri-isohexylamine, tri-n-heptylamine, triisoheptylamine, tri-n-octylamine, triisooctylamine, tri-n-decylamine, triisodecylamine, tri-n-dodecylamine, triisododecylamine, trialkylamines having straight-chain and/or branched chains having 6 to 14 carbon atoms, pyridine, α-picoline, β-picoline, γ-picoline, 2,4-dimethylpyridine (α,γ-lutidine), 2,6-di-tert-butylpyridine, 2,4,6-trimethylpyridine (collidine), triethylpyridine, quinoline, methylquinolines, ethylquinolines, mixed amines such as butyidihexylamine, dioctyldecylamine, hexyldioctylamine, dihexyloctylamine, diheptyloctylamine, didecyloctylamine, didodecyloctylamine, didodecyldecylamine, didecyldodecylamine, dioctyldodecylamine, dinonyloctylamine, dinonyidecylamine, dinonyldodecylamine and mixtures thereof.

In a large number of cases, it has proven adequate to carry out the reaction at 20° to 80° C., in particular at 30° to 60° C.

The reaction is carried out in the presence or absence of a water-insoluble solvent. The water-insoluble solvent employed can be an aliphatic hydrocarbon, a halogenated aliphatic hydrocarbon, an aromatic hydrocarbon, a halogenated aromatic hydrocarbon, an aromatic ether or a mixture of these solvents. Without claiming to be complete, water-insoluble solvents which may be mentioned at this point are hexane, heptane, octane, dichloromethane, trichloromethane, toluene, o-xylene, m-xylene, p-xylene, mixtures of isomeric xylenes, ethylbenzene, butylbenzene, chlorobenzene, o-dichlorobenzene, m-dichlorobenzene, p-dichlorobenzene, chlorotoluene, m-chlorotoluene, p-chlorotoluene, biphenyl, diphenylmethane or diphenyl ether. Mixtures of these solvents can also be used.

The reaction can be carried out in the absence or presence of a phase-transfer catalyst.

In individual cases, for example for the purpose of improving the mixing, minimizing the use and consumption of dialkyl sulfate and/or increasing the reaction rate, it can be helpful to carry out the reaction in the presence of a phase-transfer catalyst. Customarily, the phase-transfer catalyst used is a quaternary ammonium or phosphonium salt or mixtures thereof, in particular a quaternary ammonium salt of the formula

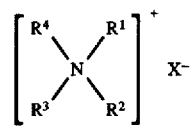

in which $R^1$, $R^2$, $R^3$ and $R^4$ are identical or different and are hydrocarbon radicals having a total of 10 to 50 carbon atoms and $X^-$ is a halide ion, hydrogen sulfate ion or hydroxyl ion, in particular a chloride, bromide or hydrogen sulfate ion, or a mixture of quaternary ammonium salts of this type.

Suitable phase-transfer catalysts are tetra($C_1$–$C_{20}$) alkylammonium salts, tri($C_1$–$C_{20}$)alkylbenzylammonium salts or di($C_1$–$C_{20}$)alkyidibenzyl-ammonium salts whose benzyl radical is unsubstituted or substituted by Cl., Br, ($C_1$–$C_4$)alkyl or ($C_1$–$C_4$)alkoxy, in particular unsubstituted.

Phase-transfer catalysts which can be employed are those which are described, for example, in DE Offenlegungsschrift 2 634 419, DE Offenlegungsschrift 3 120 912 and DE Offenlegungsschrift 3 737 919, for example tetrabutylammonium bromide, tetramethylammonium chloride, tetramethylammonium hydrogen sulfate, benzyldodecyldimethyl-ammonium chloride, stearyidimethylbenzylammonium halide, hexadecyltrimethylammonium halide, or a quaternary ammonium halide containing one or more, in particular one or two, coconut($C_{10}$–$C_{18}$)alkyl radicals, for example dicoconut($C_{10}$–$C_{18}$)alkyldimethylammonium halide or dimethylbenzylcoconut($C_{10}$–$C_{18}$)alkylammonium halide, the halide in particular being chloride or bromide. Dimethylbenzylcoconut($C_{10}$–$C_{18}$)alkylammonium chloride having an average molecular weight of 382.5, which is preferably used as a 50% strength aqueous solution (Dodigen 226), has proven particularly suitable here.

The phase-transfer catalyst is customarily employed in an amount of from 0.05 to 10, in particular 0.2 to 2.5, preferably 0.25 to 1.5, % by weight, based on the aqueous phase.

The base employed is an aqueous solution and/or a suspension of an alkali metal hydroxide or alkaline earth metal hydroxide, in particular an LiOH, NaOH or KOH solution, preferably an aqueous NaOH or KOH solution, or a mixture of these aqueous solutions. The aqueous solution and/or suspension customarily contains 5 to 50, in particular 10 to 40, preferably 20 to 35, % by weight of alkali metal hydroxide or alkaline earth metal hydroxide.

In a number of cases, it has proven useful to carry out the reaction at a pH from 6 to 10, in particular at a pH from 7 to 8.5.

Adhering to the abovementioned reaction conditions, the process can be carried out without great industrial outlay.

Water, the aromatic carboxylic acid (compound of the formula (2)), the water-insoluble tertiary amine and, if appropriate, the water-insoluble solvent are initially introduced in any desired sequence and the desired pH is then set with stirring by addition of base. An aqueous solution of the aromatic carboxylic acid or an aqueous solution of a salt of the aromatic carboxylic acid can also be employed. It is also possible to employ in the reaction a mixture consisting of water, the aromatic carboxylic acid, the water-insoluble tertiary amine and, if appropriate, the water-insoluble solvent, which mixture originates, for example, from a preceding reaction step. In this case, the desired pH is likewise set with stirring by addition of base.

The sulfate of the formula $(RO)_2SO_2$ and the base are then added at such a rate that the prestated pH is adhered to.

The water-insoluble tertiary amine can be used in a wide range of amounts. Customarily, the water-insoluble tertiary amine and the aromatic carboxylic acid (compound of the formula (2)) are employed in a molar ratio of (0.01 to 10):1, in particular (0.05 to 3):1, preferably (0.05 to 1):1, particularly preferably (0.1 to 0.5):1. The amount of water can be selected within wide ranges. The ratio of the volume of the aqueous phase to the volume of the organic phase is customarily (0.05 to 50):1, in particular (0.05 to 20):1, preferably (0.1 to 10):1.

In this connection, it is to be pointed out that the organic phase contains not only the water-insoluble tertiary amine but also the useful product, namely the compound of the formula (1) and, if appropriate, the water-insoluble solvent.

The water-insoluble solvent and the aromatic carboxylic acid (compound of the formula (2)) are employed in a weight ratio of (0.05 to 100):1, in particular (0.3 to 10):1, preferably (0.8 to 5):1.

The sulfate of the formula $(RO)_2SO_2$ is employed, based on each group R to be introduced into the compound of the formula (2), in the ratio (1 to 10):1, in particular (1.1 to 5):1, preferably (1.2 to 1.5):1. If the material employed, apart from the compound of the formula (2), additionally contains further substances which react with the sulfate, the amount of sulfate is to be increased accordingly.

It goes without saying that when handling the sulfate, in particular when handling dialkyl sulfates, more precisely dimethyl sulfate, the appropriate safety precautions are to be observed.

1 to 1.5, in particular 1.01 to 1.2, preferably 1.01 to 1.1, equivalents of base are employed per mole of sulfate of the formula $(RO)_2SO_2$ which is reacted with the compound of the formula (2). After completion of the reaction, care is taken that sulfate still present is decomposed, for example by addition of aqueous alkali, aqueous ammonia or an aqueous ammonium salt solution.

The organic phase which contains the useful product is then separated from the aqueous phase and the organic phase is worked up, for example by distillation.

If desired, however, the water-insoluble solvent can also be added after completion of the reaction in order, for example, to facilitate phase separation.

The process can be carried out continuously or batchwise. It allows both working under reduced pressure and at atmospheric pressure or elevated pressure.

The following examples describe the present invention without restricting it thereto.

EXPERIMENTAL SECTION

EXAMPLE 1

Preparation of methyl 4-hydroxybenzoate and methyl 4-methoxybenzoate

The reaction proceeds according to the following reaction scheme:

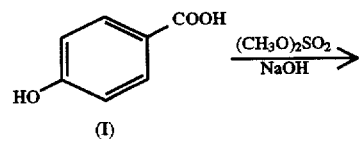

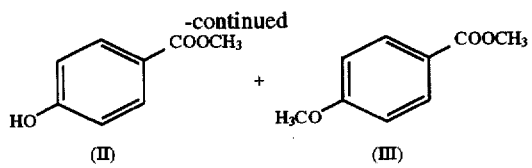

34.5 g (0.25 mol) of 4-hydroxybenzoic acid (I) and 150 g of water are initially placed in a glass flask and mixed. The 4-hydroxybenzoic acid is partially dissolved, a milky turbid suspension being formed. 5 g of a mixture of trialkylamines having 8 to 10 carbon atoms per alkyl radical (Hostarex A327, a commercial product of HOECHST AG) are dissolved in 30 g of xylene and this solution is added to the suspension and warmed to 45° C. The pH is checked by means of a calibrated pH electrode which dips into the aqueous phase. A pH of 8 is set by dropwise addition of a 10% strength by weight aqueous NaOH solution. 88.2 g (0.7 mol) of dimethyl sulfate are then added dropwise in the course of 3 hours with intensive stirring. The pH is kept within a range from 7.5 to 8.5 by dropwise addition of aqueous NaOH (10% by weight). After the end of the addition of dimethyl sulfate, the mixture is stirred overnight. Two phases are formed: an upper organic phase which contains the useful product (mixture of methyl 4-hydroxybenzoate (II) and methyl 4-methoxybenzoate (III)) and a lower, aqueous phase.

The organic phase is separated off. According to HPLC analysis, beside 15% solvents (xylene and tertiary amines) it contains 40% (corresponding to 14.7 g≙0.089 mol; 35.4% of theory) of methyl 4-methoxybenzoate and 44% (corresponding to 16.2 g≙0.106 mol; 42.4% of theory) of methyl 4-hydroxybenzoate. In the water phase—determined as HPLC area %, calculated without water and without salt contents—there is 51% of starting material (4-hydroxybenzoic acid), 37% of methyl 4-hydroxybenzoate and 11.6% of methyl 4-methoxybenzoate. By-products are only found to a very small extent (<1%). The selectivity of the formation of (methyl 4-hydroxybenzoate+methyl 4-methoxybenzoate) is ≧95%.

If the reaction is carried out at 35° to 40° C. while keeping the pH constant at 7 to 7.5 using the abovementioned starting substances and amounts, 77.2 g of organic phase are obtained. This organic phase contains (determined by means of HPLC analysis) 39.4 g (0.239 mol≙95.4% of theory) of methyl 4-methoxybenzoate and 0.8 g (0.005 mol≙2.1% of theory) of methyl 4-hydroxybenzoate. The aqueous phase contains only traces of 4-methoxybenzoic acid.

EXAMPLE 2

Preparation of methyl 3-methoxy-2,4,5-trifluorobenzoate a) Preparation of 3-hydroxy-2,4,5-trifluorobenzoic acid by decarboxylation of 4-hydroxy-3,5,6-trifluorophthalic acid The reaction proceeds according to the following equation:

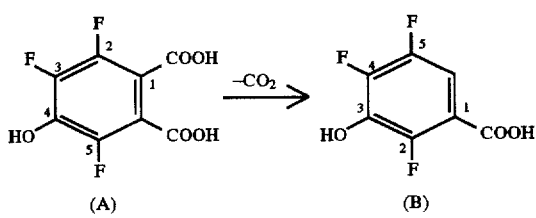

255 g of an aqueous solution which contains 20.6 g (87.3 mmol) of 4-hydroxy-3,5,6-trifluorophthalic acid (A) are initially introduced into a glass flask with stirring and treated with 20 g of a mixture of trialkylamines having 8 to 10 carbon atoms per alkyl radical (Hostarex A327; a commercial product of HOECHST AG). 49 g of a 30% strength by weight aqueous hydrochloric acid are added while mixing well. The pH is checked by means of a calibrated pH electrode which dips into the aqueous phase. After addition of the hydrochloric acid, the pH is 5. The reaction mixture is then heated to 105° C. while mixing well, the pH is kept constant at pH=6 by addition of a total of 13.5 g of a 30% strength by weight aqueous hydrochloric acid and the mixture is allowed to react for 7 hours. As a result of the decarboxylation which takes place during the course of this the 4-hydroxy-3,5,6-trifluorophthalic acid (A) is converted into 3-hydroxy-2,4,5-trifluorobenzoic acid (B).

b) Preparation of methyl 3-methoxy-2,4,5-trifluorobenzoate The reaction proceeds according to the following equation

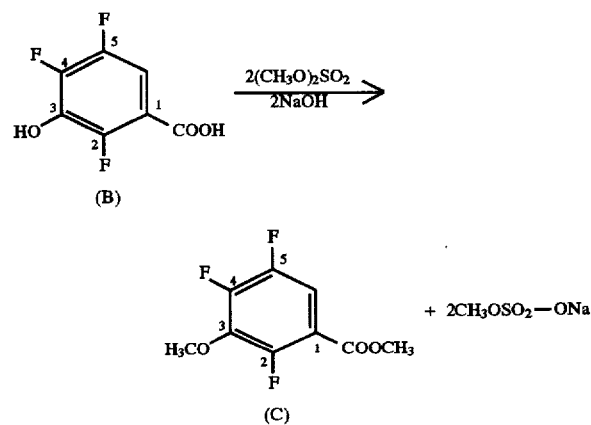

The reaction mixture obtained from Example 2a), which contains 3-hydroxy-2,4,5-trifluorobenzoic acid (B), is treated with stirring with 34 g of a 10% strength by weight aqueous sodium hydroxide solution. By means of a calibrated pH electrode which dips into the aqueous phase, the pH of the reaction mixture containing the water, the mixture of water-insoluble trialkylamines having 8 to 10 carbon atoms per alkyl radical (Hostarex A 327) and the aromatic carboxylic acid, namely 3-hydroxy-2,4,5-trifluorobenzoic acid, is checked. After addition of the sodium hydroxide solution, the pH is 7. A total of 90 g (0.72 mol) of dimethyl sulfate is then added dropwise at a temperature of 40° C. over a period of 80 minutes and the pH is kept constant at 7 by addition of a total of 37 g of a 10% strength by weight aqueous sodium hydroxide solution. 20 g of diphenylmethane are then added and the organic phase (50 g) is separated off from the aqueous phase.

The organic phase contains, determined by calibrated (HPLC) liquid chromatographic analysis, 17.6 g (80 mmol) of methyl 3-methoxy-2,4,5-trifluorobenzoate corresponding to 91.6% yield over 2 stages, based on 4-hydroxy-3,5,6-trifluorophthalic acid employed.

c) If Example 2b) is repeated, but the abovementioned amount of diphenylmethane is already added during the methylation, 17.4 g (79 mmol) of methyl 3-methoxy-2,4,5-trifluorobenzoate are obtained corresponding to 90.5% yield, based on 4-hydroxy-3,5,6-trifluorophthalic acid employed.

COMPARISON EXAMPLE

Preparation of methyl 3-methoxy-2,4,5-trifluorobenzoate without addition of a water-insoluble tertiary amine The reaction proceeds according to the following reaction scheme:

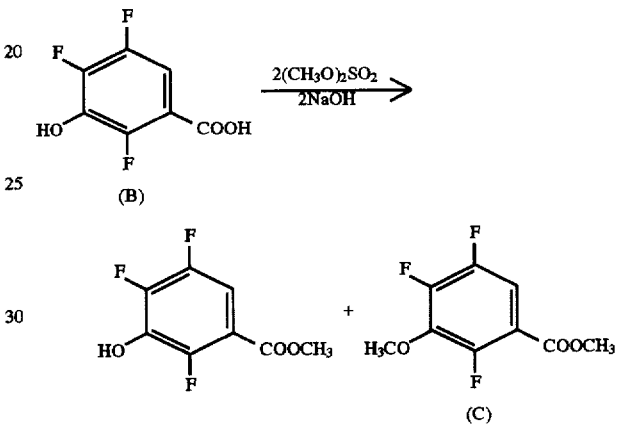

299 g of an aqueous solution which contains 15.6 g (81 mmol) of 3-hydroxy-2,4,5-trifluorobenzoic acid (B) are initially introduced into a glass flask with stirring and are treated with 10 g of xylene instead of the water-insoluble trialkylamine or amine mixture. A 30% strength by weight aqueous hydrochloric acid is added up to a pH of 7 and the pH is checked by means of a calibrated pH electrode which dips into the aqueous phase. A total of 156.8 g (1.41 mol) of dimethyl sulfate are then added dropwise at a temperature of 40° C. over a period of 3.5 hours and the pH is kept constant at 7 by addition of a total of 46.6 g of a 10% strength by weight aqueous sodium hydroxide solution. Despite a considerable excess of dimethyl sulfate, the dimethylated product, namely methyl 3-methoxy-2,4,5-trifluorobenzoate, is only formed in small amounts. 3-Hydroxy-2,4,5-trifluorobenzoic acid (B) corresponding to a yield of 8.6%, methyl 3-hydroxy-2,4,5-trifluorobenzoate corresponding to a yield of 67% and methyl 3-methoxy-2,4,5-trifluorobenzoate (C) corresponding to a yield of only 8.7% are found, in each case based on 3-hydroxy-2,4,5-trifluorobenzoic acid employed.

The problem of low formation of methyl 3-methoxy-2,4,5-benzoate can be solved by addition of a small amount (2 g) of the mixture of various water-insoluble trialkylamines used in Example 2b).

2 g of the mixture of trialkylamines mentioned in Example 2b) are added to the reaction mixture obtained from the comparison example described above and the mixture is warmed to 40° C. 18.7 g (0.168 mol) of dimethyl sulfate are added via a dropping funnel over a period of 2 hours and the pH is kept at 7 by addition of 6.4 g of a 10% strength by weight aqueous sodium hydroxide solution.

3-Hydroxy-2,4,5-trifluorobenzoic acid can then no longer be detected. However, 15.6 g (70.9 mmol) of methyl 3-methoxy-2,4,5-trifluorobenzoate, corresponding to a yield of not less than 87% of theory, have been formed.

The somewhat lower yield in comparison to Example 2b) is to be attributed to the pretreatment of the reaction mixture.

EXAMPLE 3 a) Preparation of 2,3,4,5-tetrafluorobenzoic acid by decarboxylation of tetrafluorophthalic acid The reaction proceeds according to the following equation:

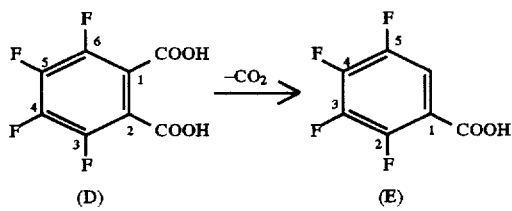

2206 g of a water-containing mixture (water content 8.3% by weight), which contains 311 g (1.31 mol) of tetrafluorophthalic acid (D) in a mixture of 150 g of trialkylamines having 8 to 10 carbon atoms per alkyl radical (Hostarex A327), 100 g of diphenylmethane and 300 g of xylene, are initially introduced with stirring into a glass flask.

The pH is adjusted to 6 to 7 using 96% strength sulfuric acid and the mixture is heated at 110° C. for 9 hours under vigorous reflux. The mixture is then heated at 110° C. while stirring well and 97.8 g of water and 179.1 g of xylene are distilled off in the course of 2 hours. The reaction mixture remaining after distilling-off contains 234.9 g (1.21 mol corresponding to 92.4% of theory) of 2,3,4,5-tetrafluorobenzoic acid (E), determined by means of calibrated HPLC analysis.

b) Preparation of ethyl 2,3,4,5-tetrafluorobenzoate

The reaction proceeds according to the following equation

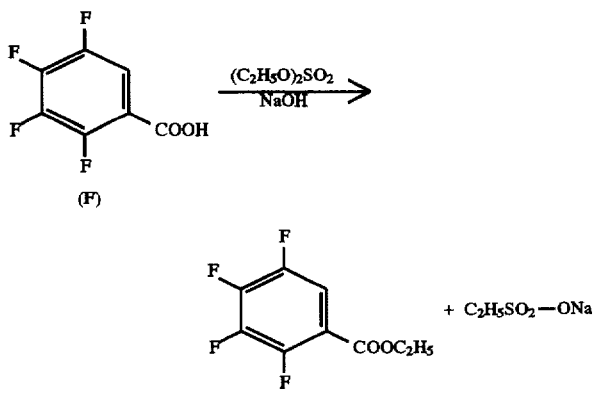

The reaction mixture obtained from Example 3a) is treated with the distillate (97.8 g of water and 179.1 g of xylene) separated off in Example 3a). 856.9 g (5.55 mol) of diethyl sulfate are then added dropwise with stirring at a temperature of 40° C. over a period of 4 hours and the pH is kept in a range from 7 to 8 by addition of aqueous sodium hydroxide solution. The mixture is stirred for 75 minutes, 10 g of ammonium chloride are added and it is stirred for 2 hours. Solid is filtered off at pH 8.2 and the aqueous phase is separated from the organic phase with addition of 600 g of xylene and 1000 g of diphenylmethane. By distillation at a temperature up to 193° C. and at a reduced pressure of 4 to 5 mbar (2 to 3 mm Hg), 1031.7 g of distillate are obtained from the organic phase (2330 g), which, determined by means of calibrated gas-chromatographic analysis, contains 245 g (1.1 mol) of ethyl 2,3,4,5-tetrafluorobenzoate, corresponding to a yield of 84% over 2 stages, based on tetrafluorophthalic acid employed.

If the reaction is carried out with 200 g of quinoline instead of with the trialkylamine mixture (Hostarex A 327), the batch proceeds completely analogously. Determined by means of calibrated HPLC analysis, 234.5 g (1.07 mol corresponding to 81.3% of theory) of ethyl 2,3,4,5-tetrafluorobenzoate are obtained. Using 300 g of collidine, the yield of ethyl 2,3,4,5-tetrafluorobenzoate is 82.1% of theory.

EXAMPLE 4

Preparation of methyl 3-methoxy-2,4,5-trifluorobenzoate (addition of a phase-transfer catalyst to assist mixing)

The reaction follows the equation mentioned in Example 2b by esterification of 3-hydroxy-2,4,5-trifluorobenzoic acid (B).

1 kg of an aqueous solution prepared analogously to Example 2a, which has been separated off from the water-insoluble amines, is treated with stirring with 10% strength by weight aqueous sodium hydroxide solution until a pH of 7.5 is established. The mixture contains 54.6 g (0.284 mol) of 3-hydroxy-2,4,5-trifluorobenzoic acid (B), determined by HPLC analysis (calibration with external standard). 20 g of Hostarex A 327 (see also Example 2b) and 20 g of a 50% strength aqueous solution of a dimethylbenzylcoconutalkyl-($C_{10}$–$C_{18}$)-ammonium chloride having an average molecular weight of 382.5 (Dodigen 226) are added with stirring by means of a magnetic stirrer. The mixture is then warmed to 50° to 52° C. and 329.2 g (2.61 mol) of dimethyl sulfate are allowed to drip in in the course of 4.5 hours and the pH of the stirred mixture is kept at 7 to 7.5 by addition of 10% strength by weight aqueous sodium hydroxide solution (consumption 133 g). The pH of the mixture containing the water, the mixture of water-insoluble trialkylamines having 6 to 8 carbon atoms per alkyl radical (Hostarex A 327) and the 3-hydroxy-2,4,5-trifluorobenzoic acid is checked by means of a calibrated pH electrode which dips into the aqueous phase.

The reaction is complete (determined by HPLC analysis) after an additional stirring time of 2 hours at pH 7 to 7.5 and 50° to 52° C. 50 g of xylene are added and the organic phase is separated off. This step is repeated twice.

The combined organic phases contain (determined by calibrated HPLC analysis) 55.5 g (0.252 mol) of methyl 3-methoxy-2,4,5-trifluorobenzoate, corresponding to a yield of 88.7% based on 3-hydroxy-2,4,5-trifluorobenzoic acid (B) employed.

We claim:

1. A process for the preparation of compounds of the formula (1)

$$R^1R^2R^3R^4R^5ArCOOR \qquad (1)$$

in which $R^1$, $R^2$, $R^3$, $R^4$ and $R^5$ are identical or different and are hydrogen, a halogen, an alkyl or alkoxy group having 1 to 6 carbon atoms, OR, NHR, $NR_2$, SR or COOR, R being an alkyl radical having 1 to 4 carbon atoms, Ar is an aryl radical having 6 to 12 carbon atoms and the radical R identified in formula (1) has the above meaning, which comprises reacting a compound of the formula (2)

$R^1R^2R^3R^4R^5ArCOOH$ (2)

in which $R^1$, $R^2$, $R^3$, $R^4$ and $R^5$ are identical or different and are hydrogen, a halogen, an alkyl or alkoxy group having 1 to 6 carbon atoms, OH, $NH_2$, NHR, SH or COOH and Ar has the same meaning as in formula (1), with a sulfate of the formula $(RO)_2SO_2$, in which R has the above meaning, at a pH from 5 to 12 in the presence of a water-insoluble tertiary amine and water at a temperature from 10° to 120° C. in the presence or absence of a water-insoluble solvent and with addition of a base.

2. The process as claimed in claim 1, wherein a compound of the formula (2) is employed in which $R^1$ and $R^2$ are identical or different and are hydrogen, an alkyl group having 1 to 6 carbon atoms, OH, $NH_2$ or COOH.

3. The process as claimed in claim 1, wherein a compound of the formula (2) is employed in which $R^1$ and $R^2$ are identical or different and are hydrogen, OH or COOH.

4. The process as claimed in claim 1, wherein a compound of the formula (2) is employed in which $R^1$ or $R^2$ is OH or COOH.

5. The process as claimed in claim 1, wherein a compound of the formula (2) is employed in which $R^1$ or $R^2$ is OH.

6. The process as claimed in claim 1, wherein a compound of the formula (2) is employed in which $R^3$, $R^4$ and $R^5$ are identical or different and are hydrogen, a halogen, or an alkyl or alkoxy group having 1 to 6 carbon atoms.

7. The process as claimed in claim 1, wherein a compound of the formula (2) is employed in which $R^3$, $R^4$ and $R^5$ are identical or different and are hydrogen, fluorine, chlorine or an alkyl group having 1 to 6 carbon atoms.

8. The process as claimed in claim 1, wherein a compound of the formula (2) is employed in which $R^3$, $R^4$ and $R^5$ are identical or different and are hydrogen or fluorine.

9. The process as claimed in claim 1, wherein a compound of the formula (2) is employed in which Ar is a phenyl radical, biphenyl radical or naphthyl radical.

10. The process as claimed in claim 1, wherein a compound of the formula (2) is employed in which Ar is a phenyl radical.

11. The process as claimed in claim 1, wherein, as sulfate of the formula $(RO)_2SO_2$, dimethyl sulfate, diethyl sulfate or dibutyl sulfate is employed.

12. The process as claimed in claim 1, wherein, as sulfate of the formula $(RO)_2SO_2$, dimethyl sulfate or diethyl sulfate is employed.

13. The process as claimed in claim 1, wherein the sulfate of the formula $(RO)_2SO_2$, based on each group R to be introduced into the compound of the formula (2), is employed in the ratio (1 to 10):1.

14. The process as claimed in claim 1, wherein, as water-insoluble tertiary amine, a trialkylamine having 4 to 20 carbon atoms per alkyl radical, a mixture of these trialkylamines, an N-containing heterocyclic compound or a mixture of the above amines is employed.

15. The process as claimed in claim 1 wherein, as water-insoluble tertiary amine, a trialkylamine having 6 to 14 carbon atoms per alkyl radical or a mixture of these trialkylamines is employed.

16. The process as claimed in claim 1, wherein, as water-insoluble tertiary amine, a mixture of trialkylamines having 6 to 12 carbon atoms per alkyl radical, which contain identical or different straight-chain or branched alkyl radicals, is employed.

17. The process as claimed in claim 1, wherein the water-insoluble tertiary amine and the compound of the formula (2) are employed in the molar ratio (0.01 to 10):1.

18. The process as claimed in claim 1, wherein the reaction is carried out at 20° to 80° C.

19. The process as claimed in claim 1, wherein the reaction is carried out at 30° to 60° C.

20. The process as claimed in claim 1, wherein, as water-insoluble solvent, an aliphatic hydrocarbon, a halogenated aliphatic hydrocarbon, an aromatic hydrocarbon, a halogenated aromatic hydrocarbon, an aromatic ether or a mixture of these solvents is employed.

21. The process as claimed in claim 1, wherein, as base, an aqueous solution of an alkali metal hydroxide or alkaline earth metal hydroxide is employed.

22. The process as claimed in claim 1, wherein the reaction is carried out at a pH from 6 to 10.

23. The process as claimed in claim 1, wherein the reaction is carried out at a pH from 7 to 8.5.

24. The process as claimed in claim 1, wherein the reaction is carried out in the presence of a phase-transfer catalyst.

25. The process as claimed in claim 1, wherein, as phase-transfer catalyst, a quaternary ammonium salt of the formula

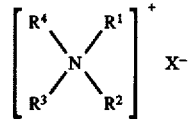

is employed in which $R^1$, $R^2$, $R^3$ and $R^4$ are identical or different and are hydrocarbon radicals having a total of 10 to 50 carbon atoms and $X^-$ is a halide ion, hydrogen sulfate ion or hydroxyl ion.

26. The process as claimed in claim 1, wherein, as phase-transfer catalyst, a tetra($C_1$–$C_{20}$)-alkylammonium salt, tri($C_1$–$C_{20}$)alkylbenzylammonium salt or di($C_1$–$C_{20}$) alkyldibenzylammonium salt whose benzyl radical is unsubstituted or substituted by Cl, Br, ($C_1$–$C_4$)alkyl or ($C_1$–$C_4$) alkoxy is employed.

27. The process as claimed in claim 1, wherein, as phase-transfer catalyst, a quaternary ammonium halide containing one or more coconut($C_{10}$–$C_{18}$)alkyl radicals is employed.

28. The process as claimed in claim 1, wherein, as phase-transfer catalyst, a dicoconut($C_{10}$–$C_{18}$)-alkyldimethylammonium halide or dimethylbenzylcoconut ($C_{10}$–$C_{18}$)alkylammonium halide is employed.

29. The process as claimed in claim 1, wherein the phase-transfer catalyst is employed in an amount from 0.05 to 10% by weight, based on the aqueous phase.

30. The process as claimed in claim 1, wherein a pH for the reaction is preselected and the reaction is carried out with addition of a base so that the preselected pH is essentially maintained throughout the reaction.

* * * * *